United States Patent [19]
Guo

[11] Patent Number: 6,086,886
[45] Date of Patent: Jul. 11, 2000

[54] COMPOSITION FOR PROMOTING INTESTINAL HEALTH

[75] Inventor: Peilin Guo, Santa Monica, Calif.

[73] Assignee: Jarrow Formulas, Inc., Los Angeles, Calif.

[21] Appl. No.: 09/177,230

[22] Filed: Oct. 22, 1998

[51] Int. Cl.[7] .................................................... A01N 65/00
[52] U.S. Cl. ...................................... 424/195.1; 435/71.1
[58] Field of Search .......................... 424/195.1; 435/71.1

[56] References Cited

U.S. PATENT DOCUMENTS

| | | | |
|---|---|---|---|
| 3,986,297 | 10/1976 | Ichimura et al. | 47/1.4 |
| 4,091,117 | 5/1978 | Mutai et al. | 426/43 |
| 4,778,766 | 10/1988 | Tanaka et al. | 436/63 |
| 5,898,198 | 1/1999 | Haber | 530/370 |

OTHER PUBLICATIONS

Derwent Computer Abstract WPIDS 97–434711 Carella et al WO 9729763, Aug. 21, 1997.
Derwent Computer Abstract WPIDS 97–434710 Carella et al WO 9729762, Aug. 21, 1997.
Derwent Computer Abstract WPIDS 78–71593A Miyaji S JP 53099371, Aug. 30, 1978.
Derwent Computer Abstract WPIDS 90–071166 Kiuchi A JP 02023848, Jan. 26, 1990.

*Primary Examiner*—Herbert J. Lilling
*Attorney, Agent, or Firm*—Cummings & Lockwood

[57] ABSTRACT

The present invention provides a composition for promoting intestinal health. The composition includes metabolites of lactic acid and propionic acid bacteria, chlorella, natural dietary fibers and botanicals. The composition suppresses the reproduction and proliferation of intestinal pathogens and is effective in removing toxic and chemotactic substances from the intestines. The composition also promotes improved bowel function.

15 Claims, No Drawings

COMPOSITION FOR PROMOTING INTESTINAL HEALTH

FIELD OF THE INVENTION

The present invention provides a composition for promoting intestinal health. More particularly, the invention provides such a composition including metabolites of lactic and propionic acid bacteria which suppresses the reproduction and proliferation of intestinal pathogens, and chlorella which binds and removes toxic and carcinogenic substances from the intestines. The composition further includes natural dietary fibers and botanicals which promote intestinal health generally and, in particular, provide improved bowel function.

BACKGROUND OF THE INVENTION

Compositions for promoting gastrointestinal health in humans are known in the art. For example, U.S. Pat. No. 5,219,904 discloses a composition including β-gluccoligosaccharide for the purpose of promoting the growth of lactic acid bacteria and improving intestinal floras.

U.S. Pat. Nos. 5,744,134 and 5,531,989 disclose compositions for restoring and maintaining gastrointestinal health comprising an immunoglobulin, and a soluble dietary fiber selected from inulin, fructo-oligosaccharides, pectin and guar gum for promoting the growth of beneficial bacteria in the intestine. In addition, the compositions may also include one or more beneficial intestinal microorganisms, such as lactic acid bacteria. These bacteria produce natural antibiotic-like bacteriocins which can inhibit pathogenic microorganisms directly, and also generate organic acids which lower the pH of the intestines and thereby inhibit the growth of undesirable, acid-sensitive bacteria.

U.S. Pat. No. 4,806,368 discloses a nutritional supplement in the form of a tablet including lactic acid bacteria and reducing compounds, such as L-cystine, to enhance the viability of the bacteria in the tablet formulation and in the intestines. The formulation further includes vitamins, minerals, lecithin, milk-derived nutrients, apple fiber and yeast extract.

The detoxifying effects of chlorella are also known in the art. For example, chlorella has been reported effective in binding and removing from the body contaminants such as heavy metals (e.g., mercury, cadmium, lead), PCBs, and dioxin.

It is an object of the present invention to provide a composition which promotes intestinal health by suppressing the reproduction and proliferation of intestinal pathogens and by removing toxic and carcinogenic substances from the intestines.

It is a further object of the invention to provide such a composition which also promotes improved bowel function.

SUMMARY OF THE INVENTION

The present invention meets these and other objects by providing a composition for promoting intestinal health which includes metabolites of lactic and/or propionic acid bacteria, and chlorella. Preferably, the metabolites are fermentation products prepared from *Lactobacillus acidophilus* and *Propionibacterium shermani*. The useful metabolites of these bacteria include organic acids, and peptides, including peptide-based cell wall constituents and natural antibiotics.

In a preferred embodiment, the composition further includes natural dietary fibers and botanicals which increase fecal weight, promote easier and more frequent bowel evacuation, and provide improved intestinal tonus and peristalsis.

DETAILED DESCRIPTION OF THE PREFERRED EMBODIMENTS

The metabolites of lactic and propionic acid bacteria included in the composition of the present invention inhibit or suppress the reproduction and proliferation of gram negative bacteria such as Pseudomonas, yeast such as Candida, and molds. These metabolites are also helpful in detoxification of the intestines and in removing from the intestines harmful compounds produced by intestinal putrefactive microorganisms. In addition, these metabolites help control gas production caused by yeast and putrefactive bacteria.

As noted above, the lactic and propionic acid bacteria metabolites found suitable for these purposes include organic acids, such as lactic, propionic and acetic acids. The metabolites further comprise peptides, including peptide-based cell wall components such as peptidoglycans, and natural antibiotics such as lactobacillin and other bacteriocins/peptides. The metabolites are fermentation products prepared from selected strains of lactic and/or propionic acid bacteria, preferably, *Lactobacillus acidophillus* and *Propionibacterium shennani*. Peptides produced by lactic and propionic acid fermentation, including cell wall peptidoglycans, are known to be inhibitory substances to many types of bacteria and have been shown to interfere with the cell walls of growing bacteria to prevent their growth. In addition, these fermentation products appear to be stimulatory to the immune system. Data indicates that fermented products from lactic acid and propionic acid bacteria can improve immune function.

In the most preferred embodiment of the invention, the composition includes a formulation of metabolic fermentation products and cell walls available from Nu-Tek Products, Inc. and sold under trademark METABOLIN. The formulation contains about 2% by weight of lactic acid, 2% by weight of propionic acid, 3% by weight of acetic acid, about 10% by weight of a blend of peptides and cell wall constituents.

The composition further comprises chlorella which provides intestinal detoxification by removing a broad spectrum of toxic and chemotactic agents from the intestines. The detoxification effect provided by chlorella is characterized by a two-phase uptake process. Binding sites present on the cell walls of chlorella permit rapid physiochemical absorption of these agents, followed by a slow but steady intracellular uptake. The chlorophyll contained in chlorella also contributes to the detoxification process, and the antioxidants in chlorella, such as chlorophyll and beta-carotene, help reduce intestinal carcinogens. Preferably, the composition includes Yaeyama chlorella (*Chlorella vulgaris*), which is particularly rich in chlorophyll.

To further promote intestinal health and, in particular, bowel function the composition further comprises selected natural dietary fibers and botanicals. Inulin-FOS is not digested by human enzymes and functions in a manner similar to soluble fiber. Inulin also promotes the growth of beneficial intestinal bacteria, in particular bifidobacteria. Other sources of fiber in the composition include beet fiber, flaxseed, psyllium husk, which contains both soluble and insoluble dietary fiber, and slippery elm bark, which contains mucilage and also is helpful in easing intestinal evacuation and removing excess intestinal mucus.

Fennel seed (*Foeniculi fructus*) is included in the composition as a source of essential oils (anethole, fenchone), terpenoid hydrocarbons (a-pene, a-phelandrene, linolene), and flavonoids. Fennel seed is effective in reducing flatulence and cramp-like pains in the gastrointestinal tract, promotes gastrointestinal motility and has a spasmolytic and carminative effect. Rhubarb root (*Rheum palmatum*) is also present in the preferred embodiment of the composition. Rhubarb root provides a source of anthroquinone and dianthrone glycosides and promotes easier intestinal evacuation.

Ginger root (*Zingiber officinale*) is included in the composition as a source of ginerols, shoganols, and phosphatidic acid. Ginger root is effective in increasing the tonus and peristalsis of the intestines. Ginger root also alleviates motion sickness due to its effect on gastric activity (as opposed to the central nervous system mechanism characteristic of conventional anti-motion sickness drugs) and also exhibits anti-ulcer effects in both animals and humans. The preferred embodiment of the composition further includes peppermint leaves (*Mentha piperita*) as a source of menthol, menthol esters and other monoterpenes. These compounds exhibit direct spasmolytic action on the smooth muscle of the digestive tract and are carminative.

Finally, the preferred embodiment of the invention includes dandelion root (*Taraxacum officinale*) which contains triterpenes, including taraxol, taraxenol and taraxasterol, and sterols. Dandelion root also provides an additional source of inulin. Dandelion root is a natural diuretic which increases bile secretion and gastric secretions and enhances bowel movement.

The composition taught by the present invention is typically incorporated into a capsule or tablet, although it should be understood that other oral dosage forms such as a powder may also be utilized. The composition is preferably ingested once or twice a day on an empty stomach, usually in the morning about one-half hour before breakfast and again in the evening about two hours after dinner. Sufficient water should be taken along with the composition; a full 8 oz glass of water being preferred.

EXAMPLE 1

The following is an example of a composition embodying the present invention. The formulation set forth below is equally divided among six capsules which constitute a single dosage of the composition.

| | |
|---|---|
| Fibers from Psyllium husk, Beet fiber and Inulin-FOS | 2 g |
| METABOLIN | 200 mg |
| Chlorella (Yaeyama) | 200 mg |
| Fennel seed | 200 mg |
| Rhubarb root | 200 mg |
| Ginger root | 100 mg |
| Slippery elm bark | 100 mg |
| Dandelion root | 80 mg |
| Peppermint leaves | 80 mg |

The formulation set forth in Example 1 was provided to eleven male and female adult subjects. Each subject ingested from 2 to 6 capsules with a full glass of water in the morning on an empty stomach and/or in the evening before sleep. Usage extended between 1 and 20 days for each subject. Subjects reported easier defecation, increased wet fecal weight and frequency of bowel movement. No side effects or complaints associated with the formulation were reported.

While preferred embodiments have been shown and described, various modifications and substitutions may be made without departing from the spirit and scope of the invention. Accordingly, it is to be understood that the present invention has been described by way of example and not by limitation.

What is claimed is:

1. A composition for promoting intestinal health, said composition comprising:

fermentation products prepared from bacteria selected from the group consisting of lactic acid bacteria, propionic acid bacteria, and mixtures thereof, said fermentation products comprising organic acids, and peptides, said peptides including peptide-based cell wall constituents of the bacteria and natural antibiotics; and chlorella.

2. The composition of claim 1, wherein the bacteria are *Lactobacillus acidophilus, Propionibacterium shermani* and mixtures thereof.

3. The composition of claim 1 further comprising natural dietary fibers and botanicals.

4. The composition of claim 1, wherein the organic acids comprise lactic acid, propionic acid and acetic acid.

5. The composition of claim 1, wherein the peptide-based cell wall constituents comprise peptidoglycans.

6. The composition of claim 1, wherein the natural antibiotics comprise lactobacillin.

7. The composition of claim 1, wherein the chlorella is *Yaeyama chlorella*.

8. The composition of claim 3, wherein the natural fibers are selected from the group consisting of psyllium husk, flaxseed, beet fiber, inulin-FOS and mixtures thereof.

9. The composition of claim 3, wherein the botanicals are selected from the group consisting of fennel seed, rhubarb root, ginger root, slippery elm bark, dandelion root, peppermint leaves and mixtures thereof.

10. A composition for promoting intestinal health, said composition comprising:

fermentation products prepared from bacteria selected from the group consisting of lactic acid bacteria, propionic acid bacteria, and mixtures thereof, said fermentation products comprising organic acids, and peptides, said peptides including peptide-based cell wall constituents of the bacteria and natural antibiotics;

chlorella; and natural dietary fibers and botanicals.

11. The composition of claim 10, wherein the bacteria are at least one of *Lactobacillus acidophilus,* and *Propionibacterium shermani.*

12. The composition of claim 10, wherein the organic acids comprise lactic acid, propionic acid and acetic acid.

13. The composition of claim 10, wherein the peptide-based cell wall constituents comprise peptidoglycans, and the natural antibiotics comprise lactobacillin.

14. The composition of claim 10, wherein the natural fibers are selected from the group consisting of psyllium husk, beet fiber, inulin-FOS and mixtures thereof.

15. The composition of claim 3, wherein the botanicals are selected from the group consisting of fennel seed, flaxseed, rhubarb root, ginger root, slippery elm bark, dandelion root, peppermint leaves and mixtures thereof.

* * * * *